United States Patent [19]

Frankel

[11] Patent Number: 4,672,960
[45] Date of Patent: Jun. 16, 1987

[54] AUTOMATIC INTUBATION DEVICE FOR GUIDING ENDOTRACHEAL TUBE INTO TRACHEA

[75] Inventor: Alfred R. Frankel, Pass-A-Grille Beach, Fla.

[73] Assignee: Renbec International Corporation, Tampa, Fla.

[21] Appl. No.: 820,664

[22] Filed: Jan. 21, 1986

Related U.S. Application Data

[63] Continuation-in-part of Ser. No. 640,843, Aug. 15, 1984, abandoned.

[51] Int. Cl.[4] ............................................. A61M 16/00
[52] U.S. Cl. ........................... 128/200.26; 128/207.14; 128/DIG. 26
[58] Field of Search .................... 128/207.14, 200.26, 128/DIG. 26, 207.15, 130; 604/26, 40, 43, 45, 49, 54, 93, 165, 264, 280, 281, 283, 284; 138/111

[56] References Cited

U.S. PATENT DOCUMENTS

| | | | |
|---|---|---|---|
| 3,744,489 | 7/1973 | Minro | 128/130 |
| 4,023,596 | 5/1977 | Tate | 138/111 |
| 4,167,946 | 9/1979 | Sandstrum | 128/DIG. 26 |
| 4,256,099 | 3/1981 | Dryden | 128/200.26 |
| 4,326,519 | 4/1982 | D'Alo et al. | 604/165 |
| 4,453,545 | 6/1984 | Inove | 128/207.15 |

*Primary Examiner*—C. Fred Rosenbaum
*Assistant Examiner*—Jerome R. Smith, Jr.
*Attorney, Agent, or Firm*—Walter J. Monacelli

[57] ABSTRACT

The automatic intubation device described herein consists of an endotracheal tube which can be inserted automatically into the trachea without the use of a laryngoscope or a physician skilled in its use and which will avoid obstructions on the way to the trachea and comprises a combination of: (1) a flexible guide comprising either a flexible tube or rod having no more than a slight curvature in the length thereof, preferably an esophageal tube, and having a male or female adaptor or track running at least a substantial portion of its length and (2) the endotracheal tube to be inserted into the trachea which endotracheal tube may have a substantial amount of curvature therein and also has a female or male adaptor or track complementary to the adaptor of the guide and designed to fit into or onto the adaptor of the guide. The guide is introduced through the mouth and pharynx to the esophagus and the endotracheal tube is guided by sliding on the adaptor of the guide to where it leaves this adaptor beyond the epiglottus and at or before reaching the entrance to the esophagus at which point curvature of the endotracheal tube bends it toward and into the trachea or where the esophagus is substantially filled or blocked by the guide the endotracheal tube is turned by the dividing wall toward the trachea. A preferred guide of this application has an oblong cross-section of appropriate width to enter the esophagus with the track or adaptor thereon being positioned in the middle of the width and adapted to position the endotracheal tube in a more accurate position to enter the trachea.

22 Claims, 35 Drawing Figures

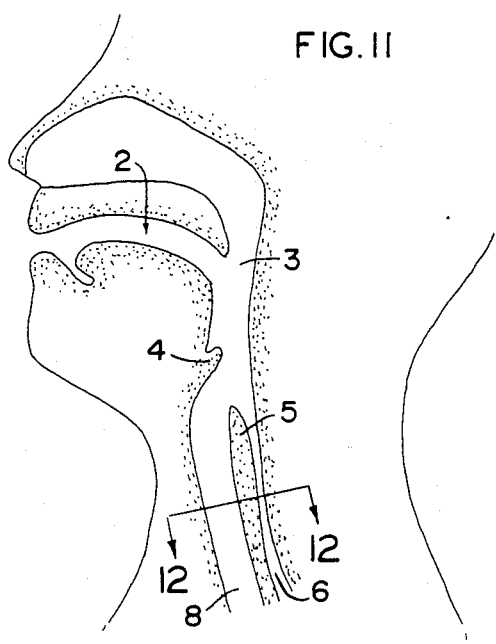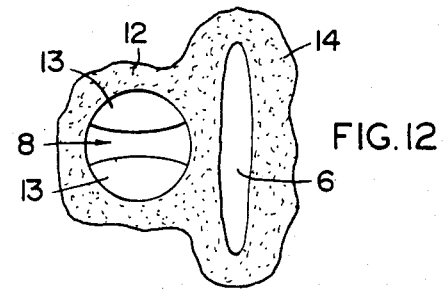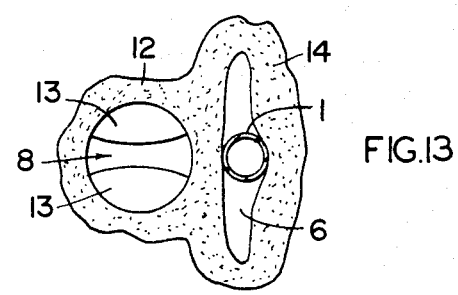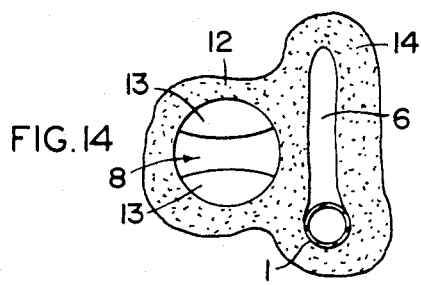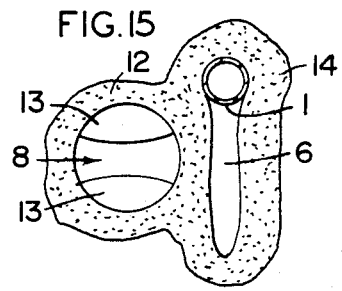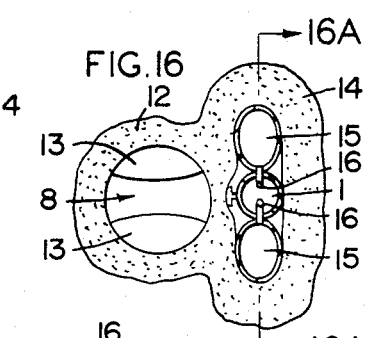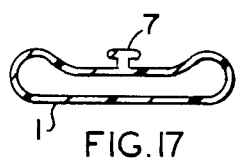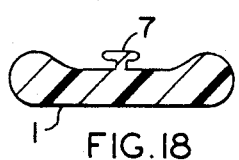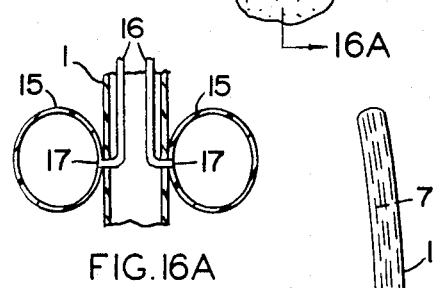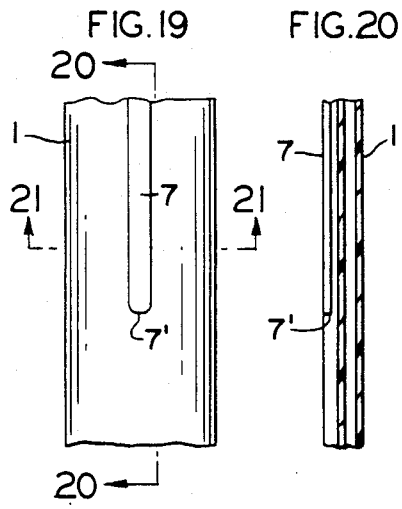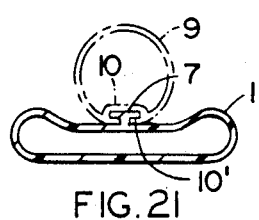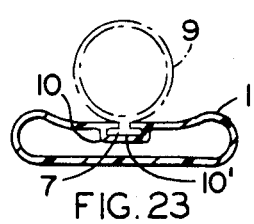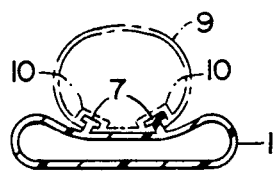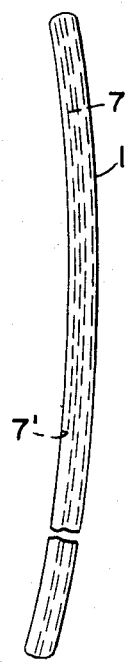

AUTOMATIC INTUBATION DEVICE FOR GUIDING ENDOTRACHEAL TUBE INTO TRACHEA

BACKGROUND OF THE INVENTION

1. Field of the Invention

This invention relates to a device for guiding an endotracheal tube into the trachea without the use of a laryngoscope. More specifically it relates to an esophageal guide adaptor or track to serve in directing the endotracheal tube into the trachea. Still more specifically it relates to an esophageal guide having a male or female adaptor running along a substantial length thereof and adapted to be fitted by a female or male complementary adaptor running lengthwise on the endotracheal tube.

2. Description of the Prior Art

Endotracheal tubes are used to provide relief for patients requiring artificial ventilation. These tubes are presently inserted by a skilled physician using a laryngoscope to displace the epiglottus and allow the physician operator to directly visualize the trachea and the vocal chords and under direct vision insert the endotracheal tube.

Attempts to blindly pass an endotracheal tube will, because of anatomical consideration, generally result in the tube being passed into the esophagus. This principle is used currently in the blind passage of esophageal airways which work by obstructing the esophagus with an inflated balloon. Then with air forced into the mouth and into the upper airway but not able to flow past the obstructing balloon in the esophagus, the air is forced into the trachea and to the lungs. However, an endotracheal tube introduced into the trachea will provide oxygen directly to the lungs and thereby is more efficient.

OBJECTIVES OF THE INVENTION

It is an objective of this invention to design a device which will permit the blind insertion of an endotracheal tube directly into the trachea by medical professionals unskilled in the use of direct laryngoscopy for the emergency insertion of endotracheal tubes.

It is also an objective of this invention to design a device consisting of an esophageal guide and a complementary endotracheal tube which will permit the blind placement of the endotracheal tube past the epiglottus, allow the endotracheal tube to be maintained in the midline and allow it to disengage itself from the esophageal guide and move anteriorly to enter the trachea.

It is also an objective to use the easy passage of the esophageal tube to assist in the passage of the endotracheal tube past the epiglottus.

Additional objectives will be obvious from the description of the invention.

SUMMARY OF THE INVENTION

In accordance with the present invention it has been found that the passage of an endotracheal tube can be guided easily and simply through the pharynx and into the trachea by inserting first an esophageal guide comprising either a tube or solid rod having an adaptor or track, either male or female, running along the outside of the esophageal guide and at least a substantial portion of the length of the esophageal guide and then introducing an endotracheal tube alongside the esophageal guide, this endotracheal tube having a female or male adaptor along the outside thereof for a portion of the length thereof with the adaptor fixed to the endotracheal tube being capable of being fitted to the adaptor or track fixed to the esophageal guide. so that the guide will serve to guide the endotracheal tube as the latter is advanced toward the trachea. The adaptors on the two tubes are complementary or reciprocal so that one will fit into or onto the other. For example, when the esophageal guide has a male adaptor on the exterior thereof, the endotracheal tube will have a female adaptor on its exterior so as to fit onto the male adaptor of the esophageal guide. Again, when the esophageal guide has a female adaptor on its exterior the endotracheal tube will have a male adaptor on its exterior which will fit into the female adaptor on the esophageal guide. In both cases as the endotracheal tube is advanced through the mouth, through the pharynx and toward the trachea, the adaptor portion thereof will slide the adaptor portion of the esophageal guide and be guided thereby.

The adaptor portion on the esophageal guide is of an appropriate length so that it will advance beyond the epiglottus and possibly beyond the dividing or separating wall between the trachea and the esophagus. With the space of the esophageal opening occupied by the guide tube, the advancement of the endotracheal tube will terminate at the dividing wall separating the esophagus and the trachea. Then the endotracheal tube is advanced until it reaches the said dividing wall, after which the guide is withdrawn. When the terminus of the adaptor passes this dividing wall, as the guide is withdrawn the endotracheal tube will slide off the terminus of the adaptor on the esophageal guide and the linear curvature of the endotracheal tube will turn this tube away from the esophagus and toward the trachea. Further advancement of the endotracheal tube assures entry of this tube into the trachea without having encountered or having been blocked by the epiglottus, and by maintaining the endotracheal tube in the midline the endotracheal tube will be allowed to move anteriorly.

For the esophageal guide the adaptor affixed or incorporated therein is positioned on the inner side of whatever linear curvature is present. With the endotracheal tube the adaptor affixed or incorporated therein is on the outer side of the linear curvature present therein. This arrangement insures that as the endotracheal tube is released from the adaptor on the esophageal guide its linear curvature will turn it toward the opening of the tracheal tube.

The position of the distal end of the esophageal guide can be determined or judged by the length of the portion introduced. In this way it is possible to determine that part of the esophageal tube at which the attached adaptor is terminated. As stated previously this terminal of the adaptor is advantageously positioned beyond the epiglottus and below the corniculate cartilage and the arytenoid muscle and cartilage which comprise the separating wall between the trachea and the esophagus. In a particular modification described hereinafter this terminal of the adaptor on the esophageal tube can have a protruding shape which will hook onto or be blocked by this dividing wall. This provides an exact determination of the positioning of this terminal and may also be used to assist in the projection of the endotracheal tube toward the trachea.

Once the distal end of the endotracheal tube has entered the trachea the esophageal guide tube can be withdrawn while or even after the endotracheal tube is further advanced into the trachea.

While it is preferred to have the adaptor or track end at a point short of the distal end of the guide, it is possible also to have the track run all the way to the distal end. In such case the operator may depend on blockage of the endotracheal tube by the dividing wall and rely on the withdrawal of the guide to release the endotracheal tube near the entrance to the trachea.

A preferred modification of this invention is one in which the esophageal tube has an oblong cross-section so that it will more truly fit the shape of the esophagus. With the esophageal tube conforming more truly to the cross-section of the esophagus, a track or adaptor positioned in the middle of one of the longer sides of the oblong will position the endotracheal tube which rides on the track more exactly in a position to enter the trachea as described more fully hereinafter.

SPECIFIC EMBODIMENTS OF THE INVENTION

The device of this invention may be illustrated by reference to the accompanying drawings in which.

FIG. 3a through 3d show cross-sections of esophageal guides with various modifications of male adaptors attached to the exterior thereof FIGS. 4a through 4d show cross-sections of endotracheal tubes with various modifications of female adaptors attached thereto adapted to the male adaptors of FIGS. 3a through 3d.

FIGS. 4e through 4h show cross-sections of endotracheal tubes with female adaptors corresponding to those in FIGS. 4a through 4d except that female adaptors are external to the tube instead of internal as in FIGS. 4a through 4d.

Figure 1:
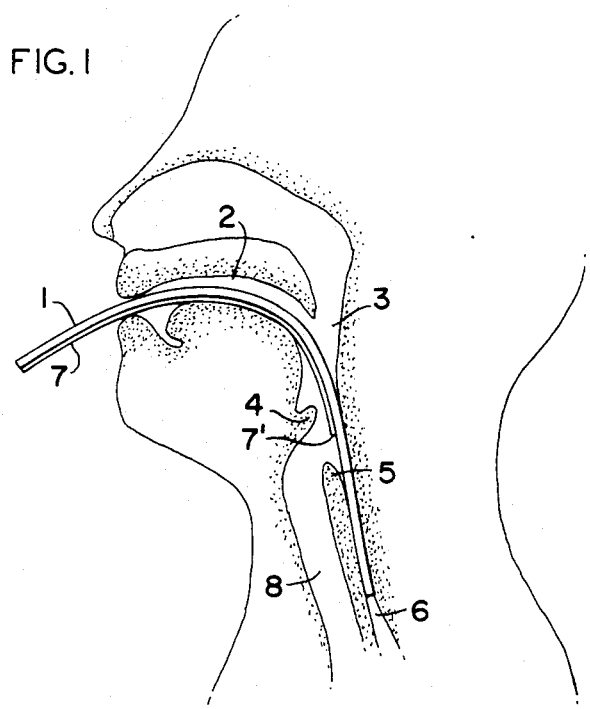
FIG. 1 is a side elevational view showing various passageways in a patient's head with a modification of the esophageal guide extending through the pharynx and into the esophagus.
Figure 3A:
Figure 3B:
Figure 3C:
Figure 3D:
Figure 5:
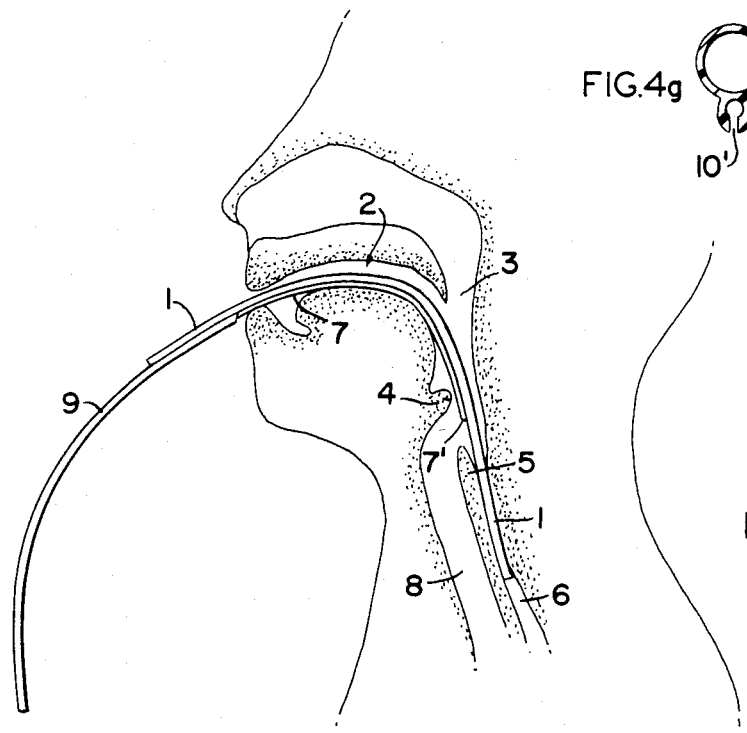

FIG. 5 is a side elevational view showing various passageways in a patient's head with the esophageal guide extending through the pharynx and into the esophagus as shown in FIG. 1 but also having an endotracheal tube about to be introduced into the mouth.

Figure 6:
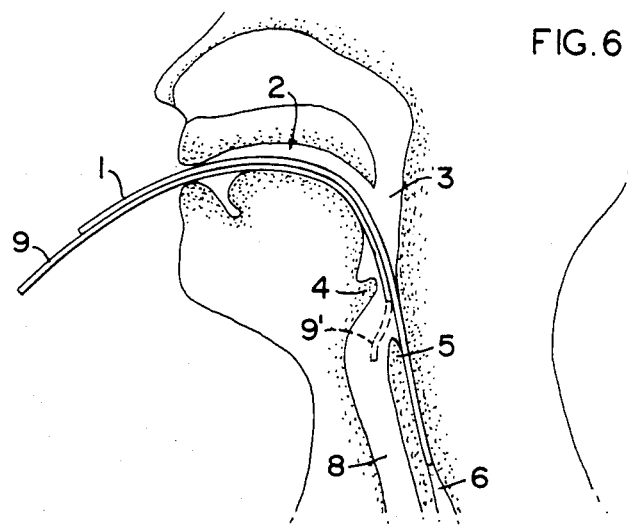

FIG. 6 shows the same view as shown in FIG. 5 with the endotracheal tube advanced further through the mouth and the pharynx with the female adaptor attached thereto fitted onto the male adaptor of the esophageal guide.

Figure 7:
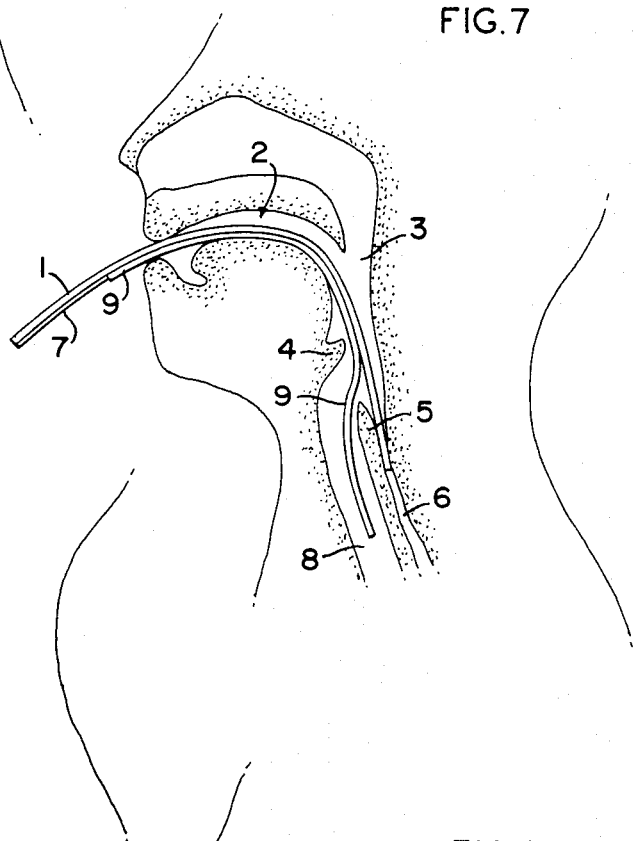

FIG. 7 shows the same view as shown in FIG. 6 with the distal end of the endotracheal tube separated from the esophageal guide and extending into the trachea.

Figure 8:
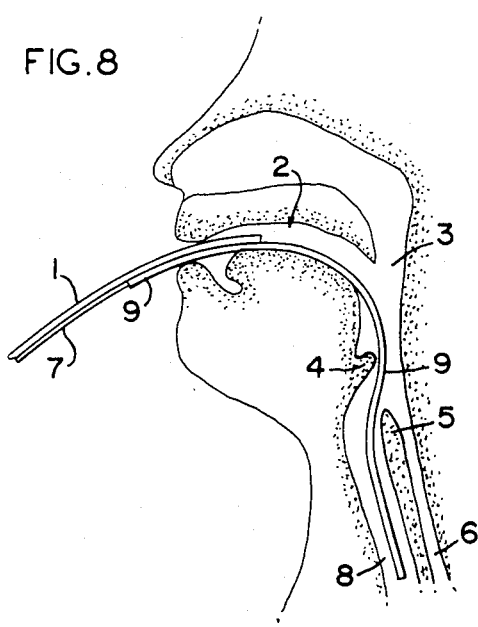

FIG. 8 shows the same view as in FIG. 7 with the distal end of the endotracheal tube extended further into the trachea and the esophageal guide substantially all withdrawn from the mouth.

Figure 9:
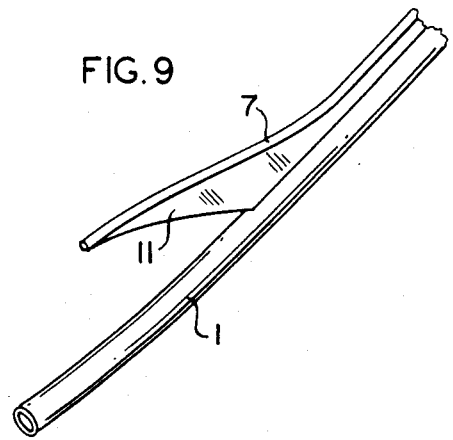

FIG. 9 shows a perspective view of an end portion of an esophageal guide which has a tracheal hook and skid extending away from the esophageal tube.

Figure 10:
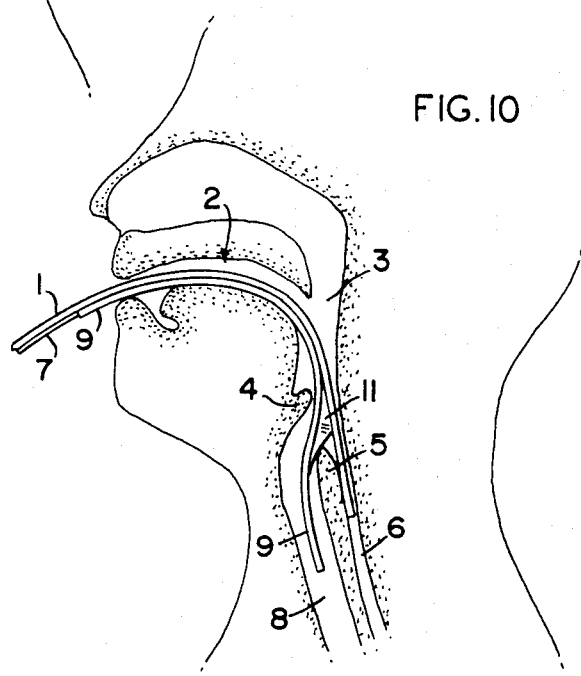

FIG. 10 shows a similar view as in FIG. 7 except that the esophageal guide has a male adaptor with the tracheal hook and skid of FIG. 9.

FIG. 11 is a side elevational view showing the various passageways in a patient's head as shown in FIGS. 1, 5–9 and 10 but without the various tubes.

FIG. 12 is a cross-sectional view of the trachea and esophagus taken at line 12—12 of FIG. 11.

FIG. 13 is a cross-sectional view similar to that of FIG. 12 except that an esophageal guide has been inserted in the preferred position directly opposite to the trachea.

FIGS. 14 and 15 are cross-sectional views similar to that of FIG. 13 except that the inserted esophageal guide is positioned to one side or the other of the trachea.

FIG. 16 is a cross-sectional view similar to that of FIG. 13 in which the inserted esophageal guide has a balloon expanded on each side thereof to insure location of the esophageal guide centrally and directly opposite the trachea.

FIG. 16A is a cross-sectional view taken at line 16A—16A of FIG. 16.

FIG. 17 is a cross-sectional view of an esophageal guide having an oblong cross-section conforming to the interior of the esophagus and having a male adaptor or track extending along a portion of the tube.

FIG. 18 is a cross-sectional view similar to that of FIG. 17 except that the esophageal guide has a solid oblong cross-section.

FIG. 19 is an elevational front view of a broken section of the oblong tube shown in FIG. 17 with a track or adaptor extending in the middle of the exterior and partway down the length of the oblong tube.

FIG. 20 is a side elevational view of the broken section of FIG. 19.

Figure 4A:
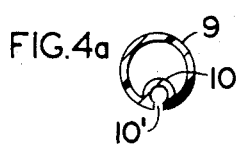
Figure 4B:
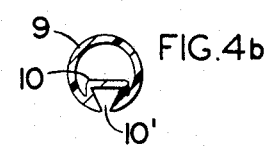
Figure 4C:
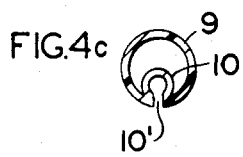
Figure 4D:
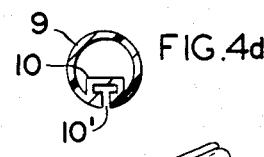

FIG. 21 is a cross-sectional view of FIG. 19 taken at line 21—21 of FIG. 19 with a cross-sectional view of an endotracheal tube of the type shown in FIG. 4a.

FIG. 22 is a cross-sectional view similar to that of FIG. 21 except that there are two male adaptors or tracks on esophageal guide 1 and two female adaptors on the endotracheal tube.

FIG. 23 is a cross-sectional view similar to that of FIG. 21 except that esophageal guide has a female adaptor and the endotracheal tube has a male adaptor.

FIG. 24 is a side view of the esophageal tube 1 showing a slight curvature through its length.

In FIG. 1 the flexible esophageal guide 1, no more than slightly curved along its length, is inserted in the patient's mouth 2 and pharynx 3 past the epiglottus 4. The corniculus or dividing wall 5 comprises the corniculate cartilage and the arytenoid cartilage which separates the trachea from the esophagus. The esophageal guide has male adaptor 7 affixed thereto and extending along a substantial portion of the length thereof with the terminus 7' positioned near the opening of the trachea 8.

Figure 2:
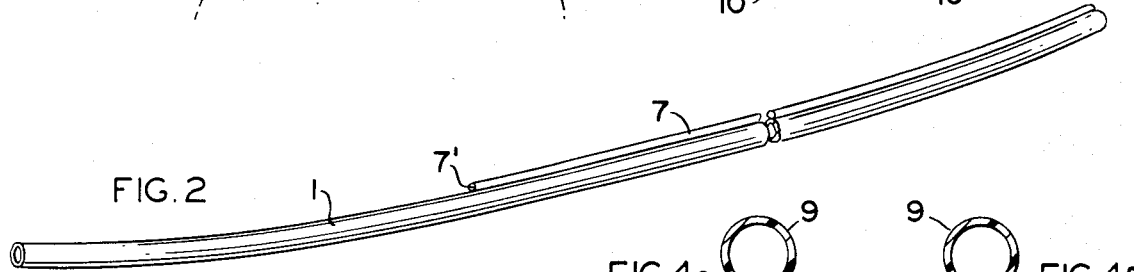
FIG. 2 is a side elevational view of an esophageal guide only slightly curved with a male adaptor affixed to and extending along a substantial portion of its length.
Figure 4E:
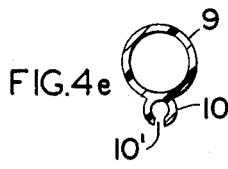
Figure 4F:
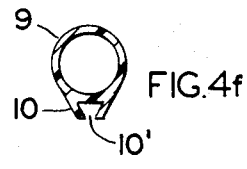
Figure 4G:
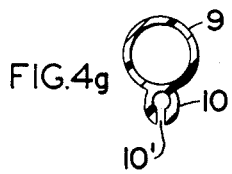
Figure 4H:
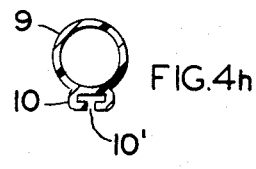

FIG. 2 is a perspective view of an esophageal guide 1 of this invention with male adaptor 7 affixed thereto and extending a substantial portion of the length thereof with terminus 7'.

FIG. 3a through 3d show cross-sections of several modifications of esophageal guides with male adaptors 7 of various shapes affixed thereto.

FIGS. 4a through 4d show cross-sections of several modifications of endotracheal tubes 9 having female adaptor sections 10 therein having shapes of openings 10' therein corresponding to the outer configurations of the male adaptors in FIGS. 3a through 3d and thereby adapted to fit thereon and to be slidably advanceable thereon so that the endotracheal tube will be guided into the desired position as the female adaptor of the endotracheal tube slides along the male adaptor of the esophageal guide.

FIGS. 4e through 4h show cross-sections of several modifications of endotracheal tubes 9 having female adaptor sections 10 attached externally to the tube with openings 10' similar in shape to those of FIGS. 4a through 4d.

FIG. 5 is a view similar to that of FIG. 1 with endotracheal tube 9, which is more curved along its length than the esophageal guide and being affixed to the esophageal guide in a preliminary position with an interior female adaptor (not shown) of the type shown in FIGS. 4a through 4d fitted over male adaptor 7 on the esophageal guide 1.

FIG. 6 is a view similar to that of FIG. 5 with the endotracheal tube 9 extended all the way to the end of adaptor 7 (not shown). When the endotracheal tube is advanced to the position shown by the dotted lines 9', the curvature of the endotracheal tube turns its distal end away from the esophageal guide and into the trachea as shown in FIG. 7.

FIG. 8 is a view similar to that shown in FIG. 7 except that the esophageal guide has been substantially withdrawn.

FIG. 9 shows a special modification of an esophageal guide of this invention with the male adaptor 7 veering sharply away from its substantially parallel attachment to the esophageal guide. This sharp veering is effected by means of fin 11 which is increased in width toward the end of adaptor 7. This fin decreases sharply in supporting width from its greatest width at the adaptor terminus to a zero width a short distance from the terminus. The fin is cut at an angle so as to form a hook as shown in FIG. 9 which will position the end of adaptor 7 far enough away from the esophageal guide to be positioned at the entrance to the trachea. This positioning gives even greater assurance that the endotracheal tube 9 will be guided directly into the trachea as shown by the view of FIG. 10.

FIG. 11 is a side elevational view showing passageways in a patient's head as shown in FIG. 1 except that the tubes shown in FIG. 1 are omitted. FIG. 12 shows a cross-sectional view of the esophagus 6 and the trachea 8 taken at line 12—12 of FIG. 11. The esophagus 6 has an oblong cross-section with esophageal wall 14. The trachea 8 has cartilogenrus ring 12 and two vocal chords 13.

In a preferred modification of the invention the esophageal guide has an oblong outer configuration. The esophagus has a cross-section as shown in FIG. 12 where the relative positioning of the trachea and the esophagus is shown. FIG. 13 shows the preferred position of the esophageal guide when it is inserted for the purposes of this invention. In this way the esophageal guide is directly opposite the trachea and the track or adaptor on which the endotracheal tube is guided will locate the endotracheal tube in appropriate position to enter the trachea. FIGS. 14 and 15 show how the esophageal guide may be positioned to one side or the other of the trachea which is undesirable for locating the endotracheal tube for entrance into the trachea. In order to insure that the esophageal guide 1 is located properly as shown in FIG. 13, the esophageal guide 1 may have balloons 15 positioned on each side of the esophageal guide, as shown so that when the end 7' of adaptor or track 7 is positioned between the epiglottus 4 and the wall 5 dividing the trachea from the esophagus the balloons may be inflated as shown in FIG. 16, so that regardless of the location of esophageal guide 1 in the esophagus the balloons will move tube 1 to a center position opposite the trachea so that when the endotracheal tube 9 leaves track or male adaptor 7, it will be positioned to enter the trachea 8. The cross-sectional view of FIG. 16A shows two small tubes inside esophageal guide 1 leading to openings 17 connecting with the interior of balloons 15. The small tubes 1 may be joined to each other above their connections to the balloons and the joined tube connected to a compressed air source, or the two individual tubes may be each connected to a compressed air source such as a compressed air cylinder.

FIG. 17 shows a cross-sectional view of a preferred oblong shaped esophageal guide 1 with track or male adaptor 7. FIG. 18 shows a similar cross-sectional view of a solid tube of similar oblong configuration.

FIGS. 19 and 20 show front and side elevational views respectfully of a broken section of the tube shown in FIG. 17. The terminus 7' of track 7 is positioned away from the lower end of tube 1 so that it may be positioned appropriately as described above with respect to FIGS. 5 and 13. With this structure the endotracheal tube coming off the end 7' of track 7 will be automatically properly centered for entrance into the trachea 8.

FIG. 21 shows a cross-section of the oblong type of esophageal guide 1 shown in FIG. 19 and 20 with an endotracheal tube 9 (also in cross-section) positioned with its female adapter 10 embracing the male adaptor or track 7 affixed to esophageal guide 1.

FIG. 22 shows a cross-section of the oblong type of esophageal guide having two tracks 7 positioned adjacent to an endotracheal tube having two female adaptors 10 of size and position to embrace the tracks 7 of the endotracheal tube. Additional such tracks and adaptors are contemplated but generally there is no added advantage with more than two such tracks and adaptors. Moreover where reference is made to "a track" or "an adaptor" it is considered that "a track" or "an adaptor" is present when there are two or more such tracks or adaptors.

FIG. 23 is a cross-sectional view of an esophageal guide 1 having a female adaptor 10 instead of the male adaptor or adaptors shown in FIGS. 21 and 22. This is complemented by having the male adaptor 7 or adaptors (track or tracks) on the endotracheal tube 9.

FIG. 24 is a side view of the esophageal guide 1 (not according to scale) showing the slight curvature in the length of the tube. Dotted lines show the track 7 hidden within the interior curvature of the width of tube as illustrated in the views of FIGS. 19 and 20.

In FIGS. 17-23, the various tubes are shown in exaggerated size in order to depict more clearly the details of these tubes. Actually the tubes described above advantageously have in the oblong cross-section a width of about ½ to 1½ inches and 1/16 to ½ inch in thickness or may be smaller or slightly larger so long as they are capable of passing without difficulty through the various passageways to be maneuvered. They may be made of materials similar to those presently used for these purposes, for example, polyethylene, polyproplene and other flexible plastic materials that will not irritate in any way the tissues with which they come into contact.

The manner of using and manipulating the esophageal guide and endotracheal tube are made clear from the above descriptions. It is important however, that the esophageal guide should be introduced and maintained with the adaptor on the inner side of the linear curvature of the tube so that as the endotracheal tube is released therefrom it will be in the appropriate position to bend toward the trachea.

While it is preferred that the adaptor attached to or incorporated in the endotracheal tube extends for a short portion of the length of the endotracheal tube, it is also possible to have this adaptor extend all the way or for only a relatively short distance from the distal end of the endotracheal tube. The purpose of this adaptor is to guide the distal end of the endotracheal tube to or near the dividing wall between the esophagus and the trachea after which the curvature of the endotracheal tube will effect a turn of the distal end toward the opening of the trachea.

The endotracheal tube adaptor may also be segmented at the end so that the tip may disengage from the esophageal guide allowing the natural curvature of the tube to bring the endotracheal tube anteriorly to the trachea while a more proximal segment of the endotracheal tube is still attached to the esophageal guide.

While reference has been made above to the desirability of locating the terminus 7' of track 7 near the opening of the trachea so that the endotracheal tube as it comes off the track will, by nature of its greater curvature, turn toward the trachea, it is also possible where the distal end of the endotracheal tube can be made to strike the upper edge of the corniculus 5 (the wall separating the trachea from the esophagus) such as by the device shown in FIG. 9 or by having the size and shape of the esophageal tube sufficient to fill the esophagus, it will not be necessary to locate the terminus 7' of track 7. Where the endotracheal tube can be made to strike the upper edge of wall 5, the track 7 can extend down into the esophagus and as the esophageal tube is withdrawn, with the endotracheal tube held in position, the endotracheal tube will be released by the withdrawal of the esophageal tube and will be allowed by its curvature to turn toward the trachea.

Instead of the oblong cross-sectional shapes shown in FIGS. 17 and 18 the esophageal tube may have a cross-sectional oblong shape more in conformance with the cross-sectional shape of the esophagus as shown in FIG. 12, that is without the bulbular portions, but with the male adaptor or track 7 or a corresponding female adaptor.

While the adaptor or tracks on the guide and endotracheal tube are shown as complementary configurations, it is also contemplated that track may also comprise a magnetic strip on the guide corresponding in position to that shown for the adaptor or track on the guide. Another magnetic strip or segments thereof may be positioned on the endotracheal tube so that the endotracheal tube may be introduced and advanced alongside an already advanced esophageal guide so that magnetic strip on the endotracheal tube may slide on the magnetic strip on the guide, keeping the tube in alignment with the guide until the endotracheal tube has approached or reached the dividing wall 5. The strengths of the magnetic fields of the respective strips should be sufficient to hold and guide the magnetic strip on the endotracheal tube so that it may slide over the magnetic strip on the esophageal guide and should not be so strong as to clutch the endotracheal tube strip so strongly as to prevent the sliding of one strip over the other.

While it may be preferred to have curvature in the endotracheal tube as described above to insure the turning of the end thereof as it leaves the distal end of the adaptor or track on the guide, it is also possible to use a flexible endotracheal tube that has little or no linear curvature and instead depend on the circumstance of having the esophagus substantially blocked or filled with the esophageal guide. In such case when the terminus of the adaptor on the guide is positioned or withdrawn to a point just outside the entrance to the esophagus, further advancement of the distal end of the endotracheal tube will result in having the dividing wall shunt the said distal end of the endotracheal tubetoward the trachea.

While certain features of this invention have been described in detail with respect to various embodiments thereof, it will of course be apparent that other modifications can be made within the spirit and scope of this invention, and it is not intended to limit the invention to the exact details shown above except insofar as they are defined in the following claims.

The invention claimed is:

1. A device for facilitating the insertion of an endotracheal tube into a patient's trachea comprising:
    (a) a flexible guide having no more than slight curvature along its length, having a size and length appropriate for insertion through the patient's mouth and pharynx and into the patient's esophagus and having a male or female adaptor extending along a substantial portion of the length thereof;
    (b) the endotracheal tube comprising a flexible tube having greater curvature along its length than that of said guide, having a size and length appropriate for insertion through the patient's mouth and pharynx into the patient's trachea and having a female or male adaptor extending along at least a portion of the length thereof, said female or male adaptor being complementary in shape and size to fit onto or into the said adaptor on said guide so as to be slidably mounted thereon, the said guide and tube being connected for use by having at least a portion of the said male adaptor inserted inside the said female adaptor.

2. The device of claim 1, in which the said adaptor on said guide is on the inner side of any linear curvature therein and the said adaptor on said endotracheal tube is on the outer side of the linear curvature thereof.

3. The device of claim 2, in which the adaptor on said guide is of male configuration and the adaptor on said endotracheal tube is of female configuration.

4. The device of claim 3, in which the said adaptor on said guide has its terminus positioned at least a short distance from the distal end of said first tube.

5. The device of claim 4, in which the terminus of the said adaptor of said esophageal tube is spaced a substantial distance from said esophageal tube and is attached to said esophageal tube by a fin which decreases sharply in supporting width from maximum at said terminus to zero width a short distance from said terminus.

6. The device of claim 1 in which said guide has two small inflatable balloons positioned on opposite sides of the said guide and linearly positioned on the guide in an area which will be positioned near the entrance to the trachea, each of said balloons being connected to and communicating with one or two tubes inside said guide leading to a pressurized gas supply for feeding pressurized gas into said balloons.

7. A process for introducing an endotracheal tube into a patient's trachea comprising the steps of:

(a) inserting through the patient's mouth and pharynx a flexible guide of appropriate size to fit comfortably and of sufficient length to reach the esophagus, said guide having no more than a slight curvature along its length and having a male or female adaptor extending on the inner side of any linear curvature thereof and extending at least a portion of the length thereof, the insertion of said guide being to a position extending into the esophagus;

(b) then fitting onto or into the said adaptor on said guide a complementary adaptor running along at least a portion of the length of an endotracheal tube which comprises a flexible tube of appropriate size to fit comfortably and of sufficient length to reach the trachea and having a curvature along its length greater than any curvature that the said guide may have, said complementary adaptor being a female or male adaptor running from the terminus of said endotracheal tube and of shape and size to fit slidably onto or into the said adaptor on said guide and extending on the outer side of said endotracheal tube;

(c) moving the distal end of said endotracheal tube into the mouth and into the pharynx, past the epiglottus and to or near the entrance to the trachea, the adaptor on said endotracheal tube sliding forward on or in the adaptor of said guide, and continuing the movement of said distal end of said endotracheal tube beyond the terminus of the adaptor on said guide when said terminus is appropriately positioned near the dividing wall between the esophagus and the trachea, whereby the curvature of endotracheal tube causes the endotracheal tube to bend toward and into the trachea, said terminus either being originally positioned in the appropriate position or being placed in such appropriate position during withdrawal of the said guide, and (d) after at least the distal end of said endotracheal tube has entered the opening of the trachea, withdrawing the said guide and thereby disengaging the endotracheal tube from the said adaptor of the said guide.

8. The process of claim 7, in which the distal end of said endotracheal tube is moved further and more completely into the trachea.

9. A device for facilitating the insertion of an endotracheal tube into a patient's trachea comprising:

(a) a flexible esophageal guide having no more than slight curvature along its length, having a size and length appropriate for insertion through the patient's mouth and pharynx and into the patient's esophagus, having an oblong cross-section and having a male or female adaptor extending along a substantial portion of the inside curvature of the length thereof;

(b) an endotracheal tube comprising a flexible tube having greater curvature along its length than that of said guide, having a size and length appropriate for insertion through the patient's mouth and pharynx into the patient's trachea and having a female or male adaptor extending along at least a portion of the length thereof, said female or male adaptor being complementary in shape and size to fit onto or into the said adaptor on said guide so as to be slidably mounted thereon, the said guide and said tube being connected for use by having at least a portion of the male adaptor inserted inside the said female adaptor.

10. The device of claim 9, in which said oblong cross-section of said guide has a bulbular portion at each end of the width thereof and a smaller thickness at the middle section of the width thereof.

11. The device of claim 9 in which said guide has a slight linear curvature on at least one of the two broad linear sides thereof.

12. The device of claim 9 in which said guide has a slight linear curvature on both of the broad linear sides thereof.

13. The device of claim 9, in which the adaptor on said first tube is of male configuration and the adaptor on said endotracheal tube is of female configuration.

14. The device of claim 13, in which the said adaptor on said guide has its terminus positioned at least a short distance from the distal end of said first tube.

15. A process for introducing an endotracheal tube into a patient's trachea comprising the steps of:

(a) inserting through the patient's mouth and pharynx a flexible guide of appropriate cross-sectional size to fit comfortably inside the esophagus and of sufficient length to reach the esophagus, said tube having an oblong cross-section, having a slight curvature along its length and having a male or female adaptor extending on the inner side of the linear curvature thereof and extending at least a portion of the length thereof, the insertion of said guide being to a position where the terminus of said adaptor on said first tube is at a point beyond the patient's epiglottus;

(b) then fitting onto or into the said adaptor on said guide a complementary adaptor running along at least a portion of the length of an endotracheal tube which has a cross-section of appropriate size to fit comfortably in the esophagus and of sufficient length to reach into the trachea and having a curvature along its length greater than any curvature that the said guide may have, said complementary adaptor being a female or male adaptor running from the distal terminus of said endotracheal tube and of shape and size to fit slidably onto or into the said adaptor on said guide and extending on the outer side of said endotracheal tube;

(c) moving the distal end of said endotracheal tube into the mouth and into the pharynx, past the epiglottus to or near the opening of the trachea, the adaptor on said endotracheal tube sliding forward on or in the adaptor of said guide, and continuing the movement of said distal end of said endotracheal tube heyond the terminus of the adaptor on said guide when said guide is appropriately positioned near the dividing wall between the esophagus and the trachea whereby the tube causes the endotracheal tube to bend toward and into the trachea, said terminus either being originally positioned in the appropriate position or being placed in such appropriate position during withdrawal of the said guide, and (d) after at least the distal end of said endotracheal tube has entered the opening of the trachea, withdrawing the said guide and thereby disengaging the endotracheal tube from the said adaptor of the said guide.

16. The process of claim 15, in which the distal end of said endotracheal tube is moved further and more completely into the trachea.

17. The process of claim 16, in which said guide is withdrawn, leaving the said endotracheal tube in the trachea.

18. The process of claim 15, in which said guide is withdrawn, leaving the said endotracheal tube in the trachea.

19. The process of claim 15, in which said oblong cross-section of said guide has a bulbular portion at each end of the width thereof and a smaller thickness at the middle section of the width thereof.

20. The process of claim 19, in which said guide has a slight linear curvature on at least one of the linear sides thereof.

21. The process of claim 15, in which both of said linear sides of said guide have slight curvature extending in substantially parallel directions.

22. The process of claim 15, in which the adaptor on said guide is of male configuration and the adaptor on said endotracheal tube is of female configuration.

* * * * *

UNITED STATES PATENT AND TRADEMARK OFFICE
CERTIFICATE OF CORRECTION

PATENT NO. : 4,672,960

DATED : June 16, 1987

INVENTOR(S) : Alfred R. Frankel

It is certified that error appears in the above-identified patent and that said Letters Patent is hereby corrected as shown below:

> On the cover page, delete "Assignee: Renbec International Corporation, Tampa, Fla."
> Col. 8, line 52, change "first tube" to read "guide".
> Col. 8, lines 54, 55 and 56, in each appearance change "tube" to read "guide".
> Col. 10, line 36, change "esophagus" to read "trachea".

Signed and Sealed this

Thirteenth Day of October, 1987

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,672,960

DATED : June 16, 1987

INVENTOR(S) : Alfred R. Frankel

It is certified that error appears in the above-identified patent and that said Letters Patent is hereby corrected as shown below:

Col. 10, line 22, change "tube" to read "guide".
Col. 10, line 54, after "whereby" insert "the curvature of".

Signed and Sealed this

Fourth Day of June, 1991

Attest:

HARRY F. MANBECK, JR.

*Attesting Officer*   *Commissioner of Patents and Trademarks*